(12) United States Patent
Rothenberger

(10) Patent No.: US 6,953,383 B2
(45) Date of Patent: Oct. 11, 2005

(54) METHOD OF DETERMINING CURRENT POSITION DATA OF A MACHINING TOOL AND APPARATUS THEREFOR

(75) Inventor: Bernd Rothenberger, Gemsbach (DE)

(73) Assignee: Sirona Dental Systems GmbH, Bensheim (DE)

(*) Notice: Subject to any disclaimer, the term of this patent is extended or adjusted under 35 U.S.C. 154(b) by 108 days.

(21) Appl. No.: 10/058,996

(22) Filed: Jan. 30, 2002

(65) Prior Publication Data

US 2002/0102916 A1 Aug. 1, 2002

(30) Foreign Application Priority Data

Jan. 30, 2001 (DE) .......................................... 101 20 341

(51) Int. Cl.[7] .............................................. B24B 49/00
(52) U.S. Cl. ............................................. 451/11; 451/5
(58) Field of Search ........................... 451/11, 8, 9, 10, 451/21, 178

(56) References Cited

U.S. PATENT DOCUMENTS 3,965,622 A * 6/1976 Stepanek ........................ 451/5
4,411,626 A * 10/1983 Becker et al. ............... 433/223
4,791,759 A * 12/1988 Komata ......................... 451/8
5,245,792 A * 9/1993 Liechti et al. .................. 451/5
6,394,880 B1 * 5/2002 Basler et al. .................. 451/28

FOREIGN PATENT DOCUMENTS

DE          40 30 175 C2    4/1997

* cited by examiner

*Primary Examiner*—Robert A. Rose
(74) *Attorney, Agent, or Firm*—Dykema Gossett PLLC

(57) ABSTRACT

Current position data is determined of a first machining tool in a machining space having a second machining tool, the second tool having known position data with regard to the position data of the first tool which are to be determined, the first tool and the second tool being movable toward and away from one another, the first tool to be determined in its position comes into contact with a machining surface, known in its position, of the second machining tool, the rotary speed of a drive motor for the second tool being set to a starting rotary speed which is so low that the rotary speed of the second tool is measurably reduced when the tool comes into contact.

22 Claims, 2 Drawing Sheets

METHOD OF DETERMINING CURRENT POSITION DATA OF A MACHINING TOOL AND APPARATUS THEREFOR

RELATED APPLICATIONS

This application relates to application Ser. No. 09/596,082, filed Jun. 16, 2000, and to application Ser. No. 10/058,996, filed Jan. 30, 2002, entitled Method of Determining Current Position Data of A Machining Tool and Apparatus Therefor, of Franz Basler, both applications commonly owned herewith. The entirety of the disclosures of both applications are specifically incorporated herein by reference.

TECHNICAL FIELD

The invention relates to a method of determining current position data of a machining tool and to an apparatus for this purpose and is to be used in particular in the production of ready-to-use tooth-restoration fitting bodies by means of grinding instruments in dental CAD/CAM grinding machines.

PRIOR ART

Grinding pencils having a surface of defined shape are especially suitable for the form-grinding of ceramic blanks. In an automated production process, it is necessary in this case to measure the position and dimension of the grinding pencil before each operation, but at least after changing the grinding pencil. This measuring can be achieved by feeling for a workpiece of known size. The feeling operation essentially comprises a grinding pencil rotating at low speed and a movement of the grinding pencil toward the workpiece or a movement of the workpiece toward the grinding pencil. The feeling operation is ended by the frictional contact between workpiece and grinding pencil, if the frictional contact has reduced the rotary speed of the grinding pencil to zero.

DE 40 30 175 C2 discloses a method of calibrating a motor-driven tool, which can be moved by means of a feed device toward and away from a workpiece to be machined, with regard to the workpiece or a holder accommodating the workpiece, and an apparatus for carrying out the method.

It has been found that the method described there reaches its limits when the shape of the frictional surfaces becomes extremely undefined of small, which, in particular in the case of grinding pencils narrowing toward the tip, can lead to considerable positioning inaccuracies during the axial feeling with the tip, since the exact shape of the tip of the grinding pencil and the distribution of the abrasive grains on the tip of the grinding pencil often vary greatly.

The object of the invention is to determine the exact linear positioning data of a tool having any desired tip geometry.

SUMMARY OF THE INVENTION

The invention is achieved with the means as claimed in claim 1. To determine the exact linear positioning data of a first grinding pencil having pronounced tapering, a second grinding pencil having a large end grinding surface is used. Firstly, the absolute positioning data of the second grinding pencil are determined by means of various feeling operations. The large end machining surface of the second grinding pencil also permits exact absolute determination of the position at a reference surface in the axial direction, since the machining surface is sufficiently large. The first and the second grinding pencils are now positioned roughly opposite one another. In the process, the axes of the grinding pencils are positioned coaxially with a sufficient offset. The second grinding pencil is now rotated at low rotary speed and the two grinding pencils are moved toward one another at the end faces. In the process, it is not important which of the two grinding pencils is moved. If the two grinding pencils strike one another, the rotation of the second grinding pencil is braked at the tip of the first grinding pencil.

In this case, the size of the offset determines the braking moment in a quite substantial manner. The absolute position of the first pointed grinding pencil can now be determined from the absolute position values of the second grinding pencil. This relative measuring is in particular very suitable in the case of a grinding operation in which a workpiece is ground with a pointed grinding pencil and with a grinding pencil having a large area at the end face.

Advantageous developments are specified in the subclaims.

In addition, an apparatus for carrying out the method has the features as claimed in claim 11. This apparatus includes a first and a second spindle for accommodating in each case at least one machining tool which can be set in rotation and has a machining surface narrowing toward the tip or respectively an end machining surface, the spindles being arranged and mounted in such a way that the machining tools and the workpiece can be moved toward and away from one another for the purpose of material removal at the workpiece. Furthermore, the apparatus also contains drive motors for adjusting the spindles and for the drive of the machining tools, and also means for producing a signal which establishes the feed path of the tool and which is used for determining the starting position of the machining tool. Owing to the fact that a contact area is formed on the apparatus by the end machining surface of the rotating tool, and that the first machining tool is oriented in an axially parallel manner with respect to the contact area with an offset, the position of the machining tool can be determined in an especially effective manner.

Advantageously, the first tool has a narrowing tip and is in this case designed in particular as a spherical grinding pencil or tapered grinding pencil with tip and the second tool is designed as an end face of a cylinder.

BRIEF DESCRIPTION OF THE DRAWING

An exemplary embodiment of the invention is shown in the drawing, in which.

DETAILED DESCRIPTION OF THE INVENTION

Figure 1:
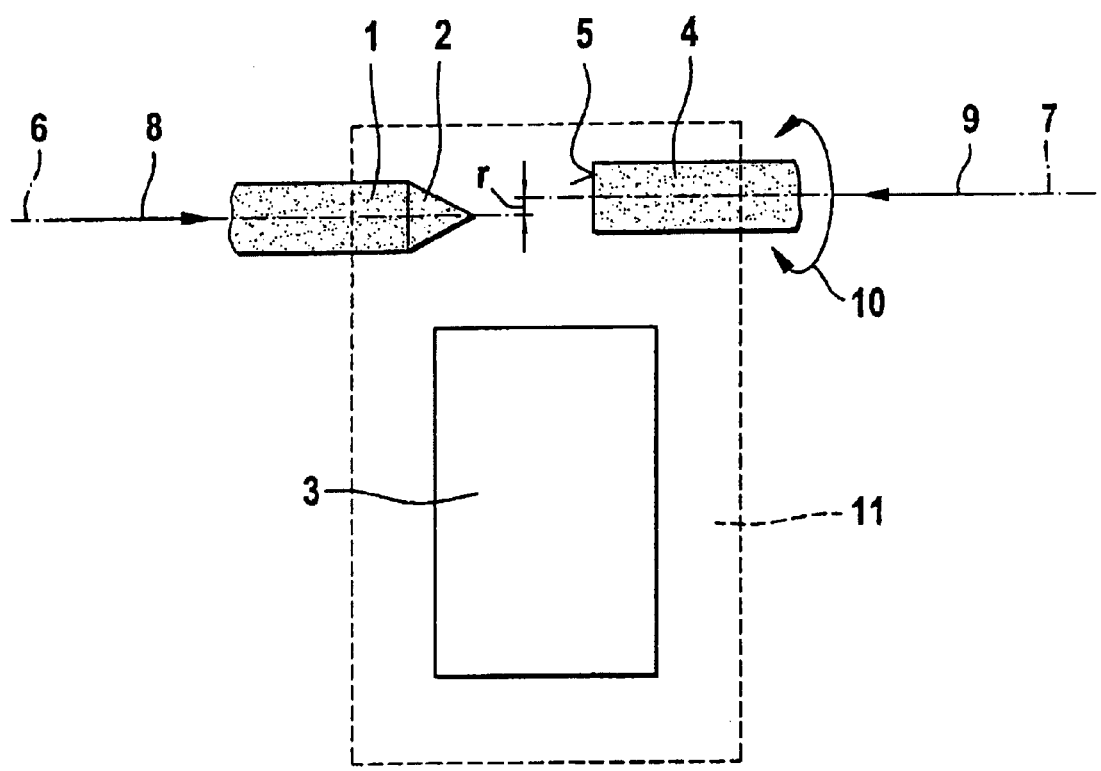
FIG. 1 shows a diagrammatic sketch of the orientation of the machining tools before the contact operation according to the invention.

The diagrammatic sketch shown in FIG. 1 shows a first machining tool 1 with a tip 2 in the form of a tapered grinding pencil which can be set in rotation via a drive shaft (not shown) for the purpose of machining a workpiece 3. To this end, a drive motor (not shown) acts on the drive shaft.

Furthermore, a machining tool 4 with a large end machining surface 5 in the form of a cylindrical grinding pencil is shown, the machining surface 5 being brought into a position opposite the tip 2 and at a distance from the workpiece 3. For the purpose of machining the workpiece 3, the machining tools 1, 4 can be moved along the axes 6, 7 and rotated about these axes, which is indicated by the arrows 8 and 9, which point in the direction of the feed, and by the arrow 10 for the rotation of the machining tool 4.

The machining tools 1 and 4, for determining the position of the tip 2 in the feed direction outside the workpiece 3 but inside a machining space 11 accommodating the workpiece, are brought into a position in which the rotation axes 6, 7 are certainly parallel to one another but have an offset r relative to one another. Before each grinding operation, the grinding pencils are positioned coaxially in such a way with the offset r for the feeling operation.

The grinding pencil 4 is then set in rotation and carefully moved at low rotary speed toward the grinding pencil 1 in the direction of the feed. In the process, it is not important which of the two grinding pencils is moved, and even both grinding pencils may be moved. If the two grinding pencils strike one another, the rotation of the second grinding pencil is braked at the tip of the first grinding pencil. In this case, the size of the offset essentially determines the braking moment. The desired braking moment $M_B$ during contact is:

$$M_B = \mu * F_{axial} * r$$

And is produced by the individual abrasive grains interlocking and thus determining the coefficient of friction $\mu$. The force $F_{axial}$ is the force with which the two machining tools act on one another in the axial direction. The braking moment is usually not known exactly; however, with just a slight introduction of axial force at a considerable offset r, the braking moment is sufficient for stopping the grinding pencil having a large area at the end face. In this case, the initial rotary speed of the grinding pencil is set so low that mutual initial damage to the grinding pencils can be ruled out. The stoppage of the grinding pencil can be detected via sensors on the motor shaft, and the current feed position can be stored.

The exact knowledge of the position data of the second machining tool is essential for the method, so that its end machining surface 5 can serve as a reference surface. The absolute positioning data of the second grinding pencil 4 are determined by means of various feeling operations. The large end grinding surface 5 of the second grinding pencil 4 also permits exact, absolute determination of the position in the axial direction, that is along the rotation axis 7, since the friction surface is sufficiently large in order to be braked by contact at a reference surface arranged, for example, on the workpiece.

The absolute position of the first pointed grinding pencil 1 can now be determined indirectly from the absolute positioning values of the second grinding pencil 4. In particular, this relative measuring is very suitable during a grinding operation in which a workpiece is ground with a pointed grinding pencil and a grinding pencil having a large area at the end face.

Via means which are not shown, the entire drive shaft and thus also the tool 1 can be moved toward and away from the workpiece 8 to be machined.

In this case, the rotary speed of the drive motor for the tool 1 is set to a starting rotary speed which is so low that, when the tool tip 7 comes into contact with the reference surface 5, the rotary speed of the drive motor becomes zero on account of the frictional forces caused by this. The drive motor is thus braked on account of friction until it comes to a stop.

It is immediately clear that this braking force in the case of a conically tapering tip has to remain very small on account of the virtually point-like contact area, so that a sufficiently large braking moment is built up only on account of the lever arm r formed by the offset, as a result of which the drive shaft comes to a stop much sooner than without an offset.

In order to avoid damage to the machining tools caused by the forces which occur during the determination of position, a preloaded spring element (not shown) is to be provided in a feed device of the drive shaft, this spring element, by spring deflection under load, absorbing the forces acting on the stationary tool. In the process, the spring deflection is effected against the direction of the feed, the preloading of the spring element having to be selected to be large enough and exceeding the envisaged loads on the tool which occur as planned during the machining. Spring deflection therefore takes place only for protecting the tool against overload. As a result, damage to the tool tip caused by overload can be avoided on the one hand, and accurate machining of the workpiece with the tool tip can be effected on the other hand.

When the drive motor is braked, care is taken to ensure that the tools 1, 4 in contact with one another at the end face do not continue to rotate. This is done by the rotary speed of the machining tool or of the drive motor being used as a command variable for the feed of the tool or tools. If the rotary speed of the tool 4 drops, the feed is reduced. If the tool 4 is braked down to zero, the feed becomes zero.

It has been found that, when determining the mutual position of two diamond grinding pencils, it is sufficient if the machining tool, before contact, is driven at a rotary speed of less than one hundredth of the rotary speed used for the machining, in particular at 1 to 10 revolutions/second.

The tools 1 and 4 are oriented with respect to one another before the actual contact for determining the position of the tool tip 2, this involving a rough determination of the position with regard to the distance apart. A slow infeed of the tools does not take place until after this rough determination of the position, which may be effected with markedly greater feed rates compared with the subsequent determination of the position, so that a shorter time is required overall.

After the determination of the position, the position established can be changed by a predetermined correction value, for example in order to take into account inertia-related system properties. As a result, the accuracy can be improved again.

Before each grinding operation, the grinding pencil is positioned axially. Care is taken to ensure that the distance between the tips of the grinding pencils is very short, so that only short feeling distances are to be covered. This can be done by a previous rough feeling operation of the machining tool 1 at a reference surface of the stationary workpiece.

The second grinding pencil 4 is then set in slow rotation (1–10 Hz). In the process, just so much power is fed to the drive motor that the friction moments of the actual bearing arrangement and of the gear grease are overcome. At the same time, the rotary speed of the grinding pencils is set so low that initial damage to the grinding pencils can be avoided.

Figure 2:
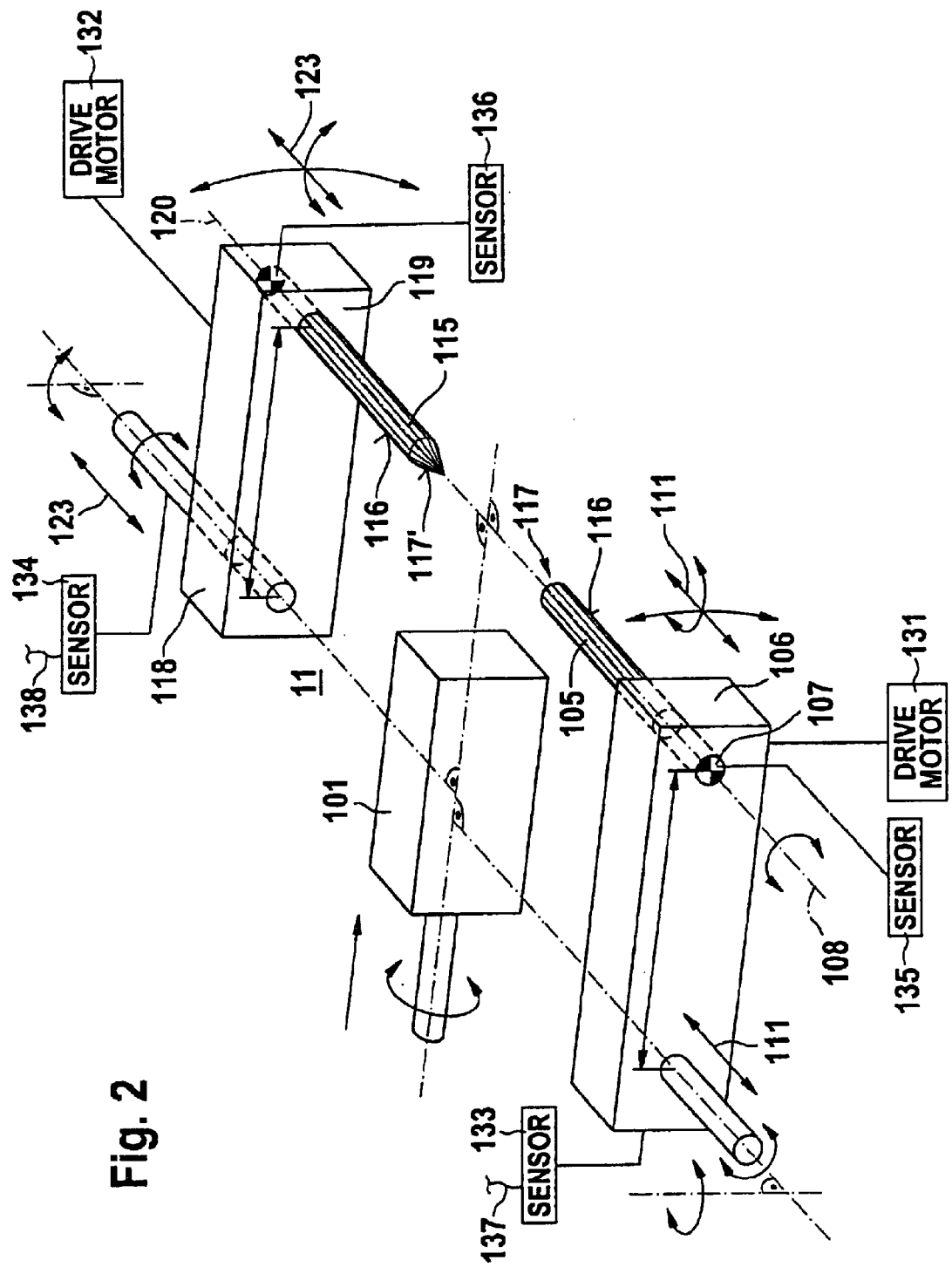
FIG. 2 shows a construction of a grinding chamber of a grinding machine incorporating the invention.

Part of a machining space 11 in a device according to the invention for production of medical fittings, in particular dental restorations, is shown in FIG. 2. A workpiece 101 is secured in a workpiece spindle (not shown). Arranged to one side of the workpiece 101, a first machining tool 105 is mounted in a tool spindle 106 and can be set in rotation by means of a drive motor 107. The machining tool 105 is designed as a cylinder grinder. The machining tool 105 rotates about a tool axis 108.

The tool spindle 106 can be moved toward and away from the workpiece 101 along the axis 108 along a first machining direction, as represented by the arrow 111.

Arranged on the other side of the workpiece 101 is a second machining tool 115 which is designed as a grinder rod with a conical point. The machining tools 105, 115 have radial working faces 116 and terminal working faces 117, 117', and, in the case of the machining tool 105 in the form of a cylinder grinder, the working face 117 is perpendicular to the tool axis 108. In the second machining tool 115, the terminal working face is designed as a cone.

The second machining tool 115 is mounted in a tool spindle 118 and can be driven by means of a drive mechanism 119 about a second tool axis 120. The tool spindle 118, and with it the second machining tool 115, can be moved along the tool axis 120 toward the workpiece 101, as indicated by the arrow 123.

The tools 105, 115 are represented in a mid position in which the tool axes 8, 20, lie in one plane. The machining tools 105, 115 are not in engagement with the workpiece 101.

To move the machining tools 105, 115 toward and away the spindles 106, 118 are connected to drive motors 131, 132. The displacement of the spindles 106, 118 in the directions of 111, 123 is measured by sensors 133,134 producing a signal transmitted via signal lines 137, 138 which establishes a feed path of the tool 115 and which is used for determining the starting position of the tool 115.

To catch the rotary speed of one of the machining tools 105, 115 sensors 135, 136 may be provided.

What is claimed is:

1. A method of determining current position data of a first machining tool in a machining space having a second machining tool, the second tool having known position data with regard to position data of the first tool which are to be determined, arranging the first tool and the second tool for movement toward and away from one another, contacting the first tool to be determined in its position with a machining surface, known in its position, of the second machining tool, setting the rotary speed of a drive motor for the second tool to a starting rotary speed which is so low that the rotary speed of the second tool is measurably reduced when the first tool comes into contact.

2. The method as claimed in claim 1, further comprising the step of establishing absolute position data of the second machining tool by means of various contact actions of the second tool at a reference surface of the workpiece or at a part fixed to the workpiece, and effecting an absolute determination of the position of the machining surface in an axial direction.

3. The method as claimed in claim 1, wherein the second tool has an end machining surface and the first machining tool has a machining surface lying at a narrowing tip.

4. The method as claimed in claim 1, wherein machining axes of the two tools are oriented parallel to one another with an offset (r), so that the first machining tool comes in contact eccentrically with the rotating machining surface of the second machining tool.

5. The method as claimed in claim 1, wherein the second machining tool, before the contact, is driven at a rotary speed of less than one hundredth of the rotary speed used for the machining.

6. The method as claimed in claim 1, wherein the tools are oriented roughly with respect to one another before the actual determination of the position.

7. The method as claimed of claim 1, wherein, during a feeling of the tool tips, so much power is fed to the drive motor that the friction moments of an actual bearing arrangement and of all lubrication are just overcome.

8. The method as claimed in claim 1, wherein the established position of the tool is changed by a predetermined correction value.

9. The method as claimed in claim 1, wherein at least one of the feed of the second tool and the feed of the first tool is coupled with rotary speed of drive motor for the second tool in such a way that a reduction in the rotary speed of the second tool brings about a reduction in the feed.

10. The method as claimed in claim 9, wherein the feed of the second tool is stopped if the rotary speed of the drive motor of the second tool becomes zero.

11. An apparatus for determining current position data of a first machining tool in a machining space having a second machining tool, the second tool having known position data with regard to position data of the first tool which are to be determined, the first tool and the second tool being arranged for movement toward and away from one another, the first tool to be determined in its position being contacted with a machining surface, known in its position, of the second machining tool, the rotary speed of a drive motor for the second tool being set to a starting rotary speed which is so low that the rotary speed of the second tool is measurably reduced when the first tool comes into contact.

12. The apparatus as claimed in claim 11, further comprising means for establishing absolute position data of the second machining tool by various contact actions of the second tool at a reference surface of the workpiece or at a part fixed to the workpiece, and means for effecting an absolute determination of the position of the machining surface in an axial direction.

13. The apparatus as claimed in claim 11, wherein the second tool has an end machining surface and the first machining tool has a machining surface lying at a narrowing tip.

14. The apparatus as claimed in claim 11, wherein machining axes of the two tools are oriented parallel to one another with an offset (r), so that the first machining tool comes in contact eccentrically with the rotating machining surface of the second machining tool.

15. The apparatus as claimed in claim 11, wherein means are provided for driving the second machining tool, before the contact, at a rotary speed of less than one hundredth of the rotary speed used for the machining, in particular at a rotary speed of 1 to 10 revolutions/second.

16. The apparatus as claimed in claim 11, wherein the tools are oriented roughly with respect to one another before the actual determination of the position.

17. The apparatus as claimed in claim 11, wherein means are provided for feeding so much power to the drive motor, during a feeling of tips of the tools, that the friction moments of an actual bearing arrangement and of all lubrication are just overcome.

18. The apparatus as claimed in claim 11, wherein an established position of the first tool is changed by a predetermined correction value.

19. The apparatus as claimed in claim 11, wherein at least one of the feed of the second tool and the feed of the first tool is coupled with rotary speed of the drive motor for the second tool in such a way that a reduction in the rotary speed of the second tool brings about a reduction in the feed.

20. The apparatus as claimed in claim 19, wherein the feed of the second tool is stopped if the rotary speed of the drive motor of the second tool becomes zero.

21. The method as claimed in claim 1, wherein the second machining tool, before the contact, is driven at a rotary speed of 1 to 10 revolutions/second.

22. The apparatus as claimed in claim 11, wherein means are provided for driving the second machining tool, before the contact, at a rotary speed of 1 to 10 revolutions/second.

* * * * *